(12) United States Patent
Tsuji et al.

(10) Patent No.: US 9,387,132 B2
(45) Date of Patent: Jul. 12, 2016

(54) DISPOSABLE ABSORBENT ARTICLE

(75) Inventors: Tomoko Tsuji, Kagawa (JP); Nobuhiro Tagawa, Kagawa (JP); Takahito Nagai, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 288 days.

(21) Appl. No.: 13/702,405

(22) PCT Filed: Jul. 25, 2011

(86) PCT No.: PCT/JP2011/004180
§ 371 (c)(1),
(2), (4) Date: Dec. 6, 2012

(87) PCT Pub. No.: WO2012/014436
PCT Pub. Date: Feb. 2, 2012

(65) Prior Publication Data
US 2013/0211354 A1     Aug. 15, 2013

(30) Foreign Application Priority Data

Jul. 26, 2010  (JP) ................. 2010-167528

(51) Int. Cl.
*A61F 13/42* (2006.01)
*A61F 13/533* (2006.01)
*A61F 13/514* (2006.01)
*A61F 13/84* (2006.01)

(52) U.S. Cl.
CPC ........... *A61F 13/42* (2013.01); *A61F 13/51496* (2013.01); *A61F 13/533* (2013.01); *A61F 13/84* (2013.01)

(58) Field of Classification Search
CPC ........................................ A61F 13/42
See application file for complete search history.

(56) References Cited

U.S. PATENT DOCUMENTS 5,611,790 A      3/1997  Osborn, III et al.
2002/0095126 A1*  7/2002  Inoue et al. ............ 604/361
(Continued)

FOREIGN PATENT DOCUMENTS

JP      5-507865 A    11/1993
JP      7-028526 U     5/1995
(Continued)

OTHER PUBLICATIONS

International Search Report and Written Opinion corresponding to PCT/JP2011/004180, dated Sep. 27, 2011.
(Continued)

*Primary Examiner* — Philip R Wiest
*Assistant Examiner* — Sara Sass
(74) *Attorney, Agent, or Firm* — Hauptman Ham, LLP

(57) ABSTRACT

A disposable absorbent article includes a chassis and a liquid-absorbent structure. The chassis has an inner sheet lying on a skin-facing side and an outer sheet lying on a garment-facing side. The outer sheet has a first outer sheet and a second outer sheet lying inside the first outer sheet. The second outer sheet is formed on its outer surface with a display area extending in a longitudinal direction. The liquid-absorbent structure is formed with a central void and lateral voids in which core material for a core is not present. The display area can be visually recognized from the garment-facing side through the first outer sheet and from the skin-facing side also through the central void of the liquid-absorbent structure.

18 Claims, 10 Drawing Sheets

(56) References Cited

U.S. PATENT DOCUMENTS

| | | | |
|---|---|---|---|
| 2003/0114818 A1* | 6/2003 | Benecke et al. | 604/378 |
| 2003/0167046 A1* | 9/2003 | Klemp | A61F 13/49012 604/383 |
| 2004/0015145 A1 | 1/2004 | Miura et al. | |
| 2006/0004333 A1 | 1/2006 | Olson | |
| 2006/0149204 A1* | 7/2006 | Niemeyer et al. | 604/385.16 |
| 2007/0049884 A1 | 3/2007 | Long et al. | |

FOREIGN PATENT DOCUMENTS

| | | |
|---|---|---|
| JP | 2002-360620 A | 12/2002 |
| JP | 2003-190210 A | 7/2003 |
| JP | 2004-298571 A | 10/2004 |
| JP | 2005-021390 A | 1/2005 |
| JP | 2005-523139 A | 8/2005 |
| JP | 2006-326221 A | 12/2006 |
| JP | 2007-097627 A | 4/2007 |
| JP | 2011-130798 A | 7/2011 |

OTHER PUBLICATIONS

Supplementary European Search Report issued Jun. 4, 2014, corresponds to European patent application No. 11812038.5.

* cited by examiner

DISPOSABLE ABSORBENT ARTICLE

RELATED APPLICATIONS

The present applications is a National Phase of International Application No. PCT/JP2011/004180, filed Jul. 25, 2011, and claims priority from Japanese Application No. 2010-167528, filed Jul. 26, 2010.

TECHNICAL FIELD

The present invention relates to disposable absorbent articles and more particularly to disposable absorbent articles such as disposable diapers, disposable toilet-training pants, disposable pants for incontinent patients, disposable menstruation pants or disposable pads each formed with a display area adapted to be visually recognized from garment-facing and skin-facing sides thereof.

BACKGROUND ART

Disposable absorbent articles each comprising an inner sheet, an outer sheet and an absorbent structure sandwiched between these inner and outer sheets wherein the article includes a display area is known. For example, PTL 1 (JP 2004-298571 A) discloses a disposable absorbent article having a display area printed as a pattern of straight heavy lines and adapted to be visually recognized from the outer side of an outer sheet and PTL 2 (JP 2002-360620 A) discloses a urine pad having printed, front-rear displaying layers adapted to be visually recognized from the inner sheet. According to the disclosures of these PTL 1 and PTL 2, the printed display area provided on the article, respectively, allows the user to distinguish the inner and outer sides of the absorbent article from each other and to distinguish the front and rear sides of the absorbent article from each other.

CITATION LIST

Patent Literature

[PTL 1] JP 2004-298571 A
[PTL 2] JP 2002-360620 A

SUMMARY OF INVENTION

Technical Problem

However, for the articles disclosed in PTL 1 and PTL 2, when it is desired to form the display area such as graphics adapted to be visually recognized not only from the inner side but also from the outer side of the article, the inner and outer sheets must be respectively provided with such display area. In consequence, a process for forming the display area such as graphics will be inevitably complicated.

Solution to Problem

According to the present invention, there is provided a disposable absorbent article which comprises a chassis having a longitudinal direction, a transverse direction, a skin-facing side and a garment-facing side and further comprises a liquid-absorbent structure containing therein an absorbent core and positioned on or within the chassis, wherein the chassis is formed with a display area which is adapted to be visually recognized from the garment-facing side and which overlaps with the liquid-absorbent structure.

A part of the liquid-absorbent structure overlapping with the display area is formed with at least one void in which the core is substantially absent so that the display area may be visually recognized from the skin-facing side through the void.

DESCRIPTION OF EMBODIMENTS

<First Embodiment>

Figure 1:
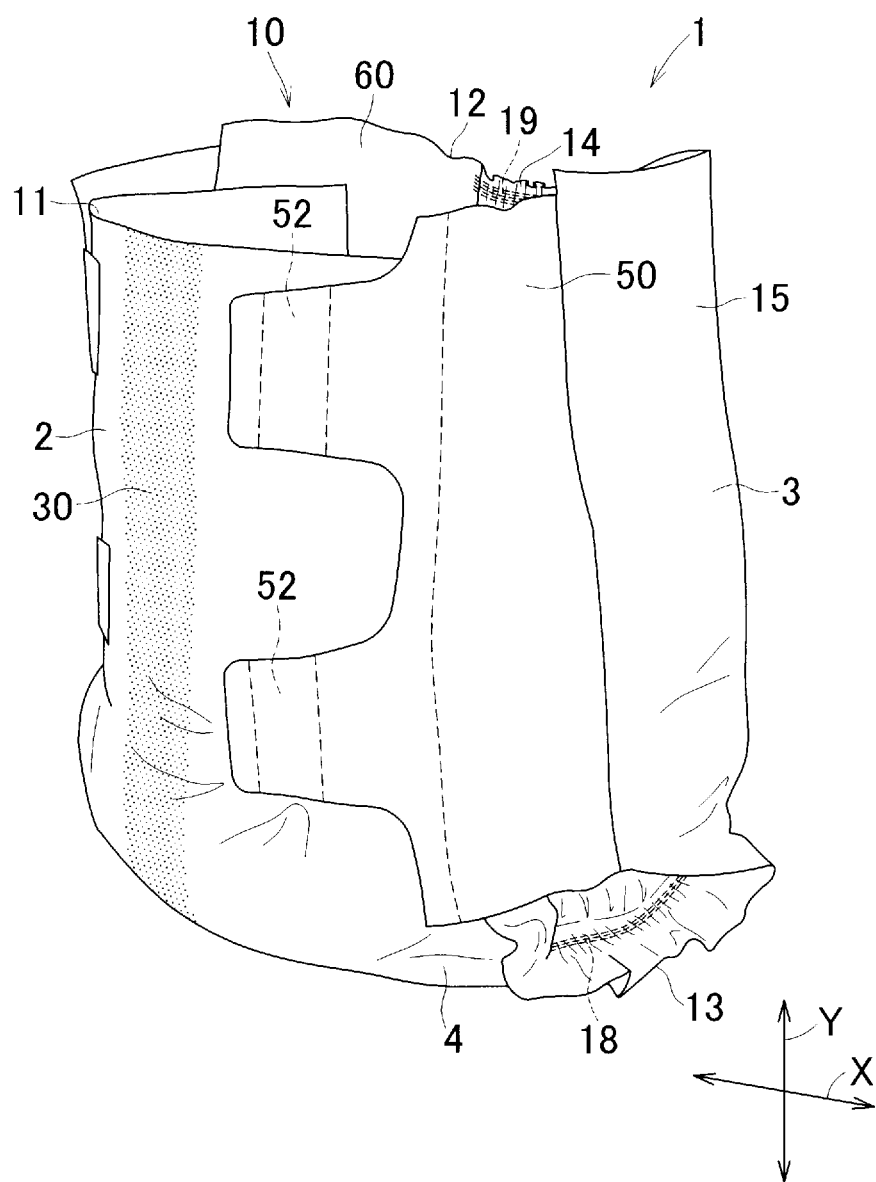
FIG. 1 is a perspective view of a diaper as an example of a disposable absorbent article according to a first embodiment of the present invention.

A diaper 1 comprises a chassis 10 having a skin-facing side, a garment-facing side, a front waist region 2 referred to hereinafter also as a first waist region, a rear waist region 3 referred to hereinafter also as a second waist region and a crotch region 4 extending between the front and rear waist regions 2, 3; a liquid-absorbent structure 20; and a pair of leakage-barrier cuffs 60 lying on the skin-facing side of the chassis 10. The diaper 1 has an imaginary longitudinal center line P-P bisecting a length dimension of the diaper 1 in a transverse direction X (i.e. bisecting the width of the diaper) and an imaginary center line Q-Q bisecting a length dimension of the diaper 1 in a longitudinal direction Y (i.e. bisecting the length of the diaper) wherein the diaper 1 is shaped almost symmetrically about the imaginary longitudinal center line P-P. The shape of the diaper and the presence of the leakage-barrier cuffs, for example, are not essential to the present invention.

The chassis 10 has front and rear ends 11, 12 extending in the transverse direction X and a pair of side edges 13 extending in the longitudinal direction Y wherein the side edges 13 concavely curve, in the crotch region 4, towards the imaginary longitudinal center line P-P so that a distance between the side edges 13 is gradually reduced towards the central region of the side edges. As will be apparent from FIG. 1, the side edges 13 in the front and rear waist regions 2, 3 are engaged with each other via side flap sheets 50 so that the front and rear ends 11, 12 of the chassis 10 may define a waist-opening and the side edges 13 in the crotch region 4 may define a pair of leg-openings.

The chassis 10 comprises an inner sheet 14 lying on the skin-facing side and an outer sheet 15 lying on the garment-facing side. The inner sheet 14 is preferably formed of a liquid-pervious fibrous nonwoven fabric and may have a basis mass (mass per unit area) of about 15 to about 35 g/m$^2$; it is specifically formed of a spun bonded fibrous nonwoven fabric which may have a basis mass of about 18 g/m² in the present embodiment.

The outer sheet 15 comprises a first outer sheet 16 being generally the same as the inner sheet 14 in shape as well as in size and a second outer sheet 17 lying on the inner side of the first outer sheet 16. The first outer sheet 16 may be formed of a spun bonded/melt blown/spun bonded (SMS) fibrous nonwoven fabric, preferably having a basis mass of about 15 to about 35 g/m²; it specifically has a basis mass of about 17 g/m² in the present embodiment. The second outer sheet 17 may be formed of an air-permeable and liquid-impervious plastic film, preferably having a basis mass of about 10 to about 25 g/m², and specifically having a basis mass of about 18 g/m² in one embodiment.

An outer surface of the second outer sheet, i.e., the surface thereof facing the first outer sheet 16, is formed with display area 30 extending in the longitudinal direction Y. The display area 30 has, for example, a color phase different from those of the first and second outer sheets 16, 17 and can be visually recognized from the garment-facing side through the first outer sheet 16. More specifically, in contrast with the first and second outer sheets 16, 17 being white, the display area 30 is blue wherein this blue display area 30 can be visually recognizable through the first outer sheet 16. The display area 30 continuously and rectilinearly extends in the longitudinal direction Y along the imaginary longitudinal center line P-P to the front and rear ends 11, 12 of the chassis 10. In other words, in a preferred embodiment, the display area 30 is formed to extend in the longitudinal direction Y over a full length of the chassis 10.

At least in the crotch region 4, two or more leg elastic elements 18 extending in the longitudinal direction Y are attached under tension and in a contractible manner between the inner and outer sheets 14, 15. Under contraction of these leg elastic elements 18, the side edges 13 of the chassis 10 come in close contact with the wearer's body and thereby prevent body waste such as urine from leaking out beyond peripheries of the leg-openings. In a similar way, in the rear waist region 3, two or more waist elastic elements 19 extending in the transverse direction X are attached under tension and in a contractible manner between the inner and outer sheets 14, 15. Under contraction of these waist elastic elements 19, the front and rear ends 11, 12 of the chassis 10 come in close contact with the wearer's body and thereby prevent body waste such as urine from leaking out beyond a periphery of the waist-opening.

While the inner sheet 14 is generally the same as the first outer sheet 16 in shape as well as in size, it is also possible to provide the inner sheet 14 of a generally rectangular shape having a length dimension in the transverse direction X (i.e. its width) smaller than that of the first outer sheet 16. In this case, it is possible to attach the leg elastic elements 18 between the leakage-barrier cuffs 60 and the outer sheet 15, more specifically, between the leakage-barrier cuffs 60 and the second outer sheet 17.

Between the inner and outer sheets 14, 15, a liquid-absorbent structure 20 is sandwiched. The liquid-absorbent structure 20 comprises a first surface 21 lying on the skin-facing side, a second surface 22 opposite to the first surface 21, a liquid-absorbent core 23 and a wrapping sheet 24 adapted to wrap the core 23. The core 23 is contoured by front and rear ends 25, 26 and side edges 27 extending in the longitudinal direction Y and may be formed of core materials such as fluff wood pulp fibers, super-absorbent polymer particles or a mixture thereof. As the wrapping sheet 24, for example, liquid-dispersant tissue paper having a basis mass of about 10 to about 25 g/m² may be used.

The liquid-absorbent structure 20 includes an elongate central void 41 and elongate lateral voids 42 in which the liquid-absorbent structure 20 is partially or completely free of the core material, meaning that it is core material-free. It should be understood that the expression "core material-free" used herein includes a case in which such void does not contain the core material at all and a case in which such void contains a slight amount of the core material but substantially does not contain the core material. The central void 41 comprises a plurality of slit-like segments intermittently extending in the longitudinal direction Y. More specifically, these slit-like segments are formed along the imaginary longitudinal center line P-P and spaced one from another in the longitudinal direction Y so that these segments lie in the front and rear waist regions 2, 3 and the crotch region 4, respectively. Each of the lateral voids 42 also comprises a plurality of slit-like segments intermittently extending in the longitudinal direction Y. More specifically, these slit-like segments are respectively formed on both sides of the central void 41 and these slit-like segments are spaced one from another in the longitudinal direction Y so that these segments lie in the front and rear waist regions 2, 3 and the crotch region 4, respectively. The present invention is not to be limited to this specific arrangement of voids, as others are envisaged. For example, the central void and/or the lateral voids may each consist of a single segment. Also, the void or voids may be slit-shaped or they may have an alternative shape, such as a rectangle, square, triangle, diamond, dot or circle.

The core 23 may be dimensioned to have a length of about 500 to about 700 mm in the longitudinal direction Y, preferably of about 600 to about 650 mm and specifically of about 620 mm in the present embodiment and a length of about 150 to about 400 mm, preferably of about 200 to about 350 mm in the transverse direction X, specifically of about 300 mm in the present embodiment. In the front waist region 2, the respective slit-like segments of the central void 41 and the lateral voids 42 may have a length of about 80 to about 120 mm, specifically of about 100 mm in the present embodiment in the longitudinal direction Y. In the rear waist region, the respective slit-like segments may have a length of about 100 to about 150 mm, specifically of about 125 mm in the present embodiment. In the crotch region 4, the respective slit-like segments may have a length of about 180 to about 220 mm, specifically of about 200 mm in the present embodiment. The slit-like segments of the voids 41, 42 lying in the front waist region 2 may be spaced from those lying in the front waist region 2 and those lying in the rear waist region 3 by about 30 to about 50 mm in the longitudinal direction Y, specifically by about 40 mm in the longitudinal direction Y in the present embodiment. A length dimension of the central void 41 in the transverse direction X (i.e. its width) is, preferably, about 5 to about 20 mm, specifically of about 9 mm and a length dimension of the respective lateral voids 42 in the transverse direction X (i.e. its width) is, preferably, about 7 to about 10 mm, specifically of about 8 mm in the present embodiment. The respective lateral voids 42 may be spaced from the central void 41 in the transverse direction X by about 40 to about 60 mm, specifically by about 50 mm in the present embodiment.

The core 23 and the wrapping sheet 24 are bonded to each other by bonding means such as hot melt adhesives (not shown) and, in the central void 41 and the respective lateral voids 42, sections of the wrapping sheet 24 on the first surface 21 and the second surface 22 are put in direct contact and bonded to each other.

The above-described liquid-absorbent 20 has its length dimensions in the longitudinal direction Y and in the transverse direction X smaller than those of the chassis 10 so that the front and rear ends 25, 26 of the core 23 are spaced inwardly in the longitudinal direction Y from the front and rear ends 11, 12 of the chassis 10, respectively. Outside the front and rear ends 25, 26 of the core 23 in the longitudinal direction Y, the core 23 is not present and the inner and outer sheets 14, 15 are directly bonded to each other to form front and rear flaps 71, 72.

Between the inner sheet 14 and the outer sheet 15, a pair of optional side flap sheets 50 are attached. These side flap sheets 50 lie in the rear waist region 3 and extend outward of side edges 13 of the chassis 10 in the transverse direction X. Hook elements 52 of the mechanical fastener serving as engagement means are attached to the side flap sheets 50 via reinforcing sheets 51. The side flap sheets 50 are further provided inboard of the reinforcing sheets 51 as viewed in the transverse direction X with two or more side flap biasing elastic elements 53 extending in the transverse direction X and attached under tension and in a contractible manner to these side flap sheets 50 to elasticize them.

The hook elements mounted on the side flap sheets 50 may be directly engaged with the first outer sheet 15 in the front waist region 2 to the pant-shaped diaper 1. The side flap sheets 50 are elasticized in the transverse direction X by the side flap elastic elements 53 so that, upon engagement of these side flap sheets 50 with the front waist region 2, the waist-opening defined by the front and rear ends of the chassis 10 is reliably put in close contact with the wearer's body. Even when the right and left side flap sheets 50 are engaged with the front waist region 2 under differently stretched states, these stretched states are equalized during use of the diaper 1 and eventually the waist-opening is evenly put in close contact with the wearer's body.

The paired leakage-barrier cuffs 60 are attached to the skin-facing side of the inner sheet 14. The leakage-barrier cuffs 60 may be formed of a hydrophobic fibrous nonwoven fabric, preferably having a basis mass of about 10 to about 25 g/m². As such a fibrous nonwoven fabric, for example, a fibrous nonwoven fabric such as a spun bonded fibrous nonwoven fabric or a spun bonded/melt blown/spun bonded (SMS) fibrous nonwoven fabric may be used, specifically, a spun bonded fibrous nonwoven fabric having a basis mass of about 25 g/m² in the present embodiment. The leakage-barrier cuffs 60 are provided to be spaced from each other in the transverse direction X wherein respective outer side edges 61 thereof are bonded to the inner sheet 14 along the side edges 13 of the chassis 10 by hot melt adhesives or the like (not shown) and respective inner side edges 62 are not bonded to the inner sheet 14 so that these inner side edges 62 may be spaced upward from the inner sheet 14. The respective inner side edges 62 are formed with sleeves within which barrier-cuff elastic elements 63 extending in the longitudinal direction Y are attached under tension and in a contractible manner. Upon contraction of these barrier-cuff elastic elements 63, the inner side edges 62 are spaced upward from the inner sheet 14, put in close contact with the wearer's skin and thereby prevent body waste such as urine from leaking out from the diaper 1.

Figure 2:
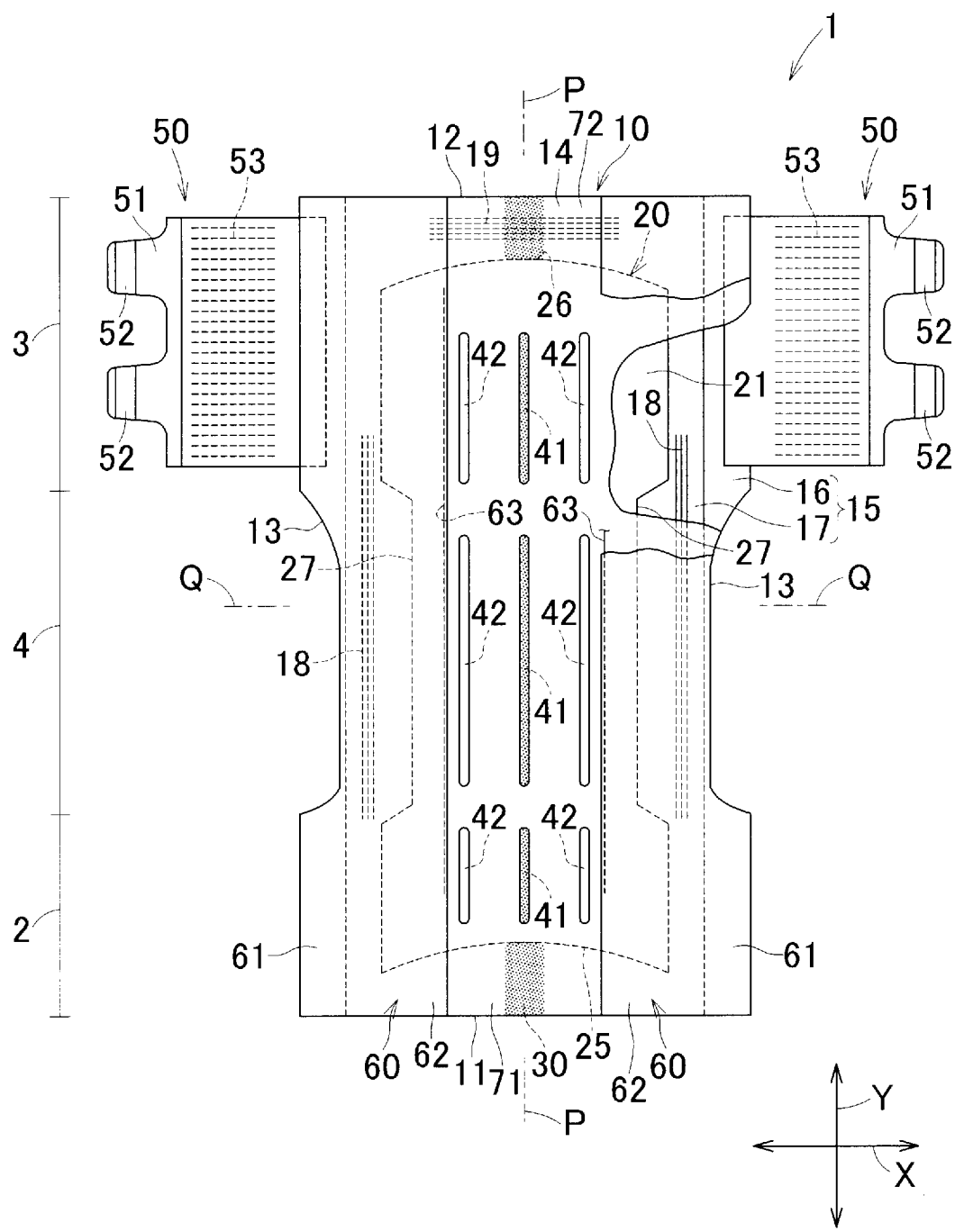
FIG. 2 is a developed plan view showing the diaper according to FIG. 1 as viewed from its skin-facing side.
Figure 3:
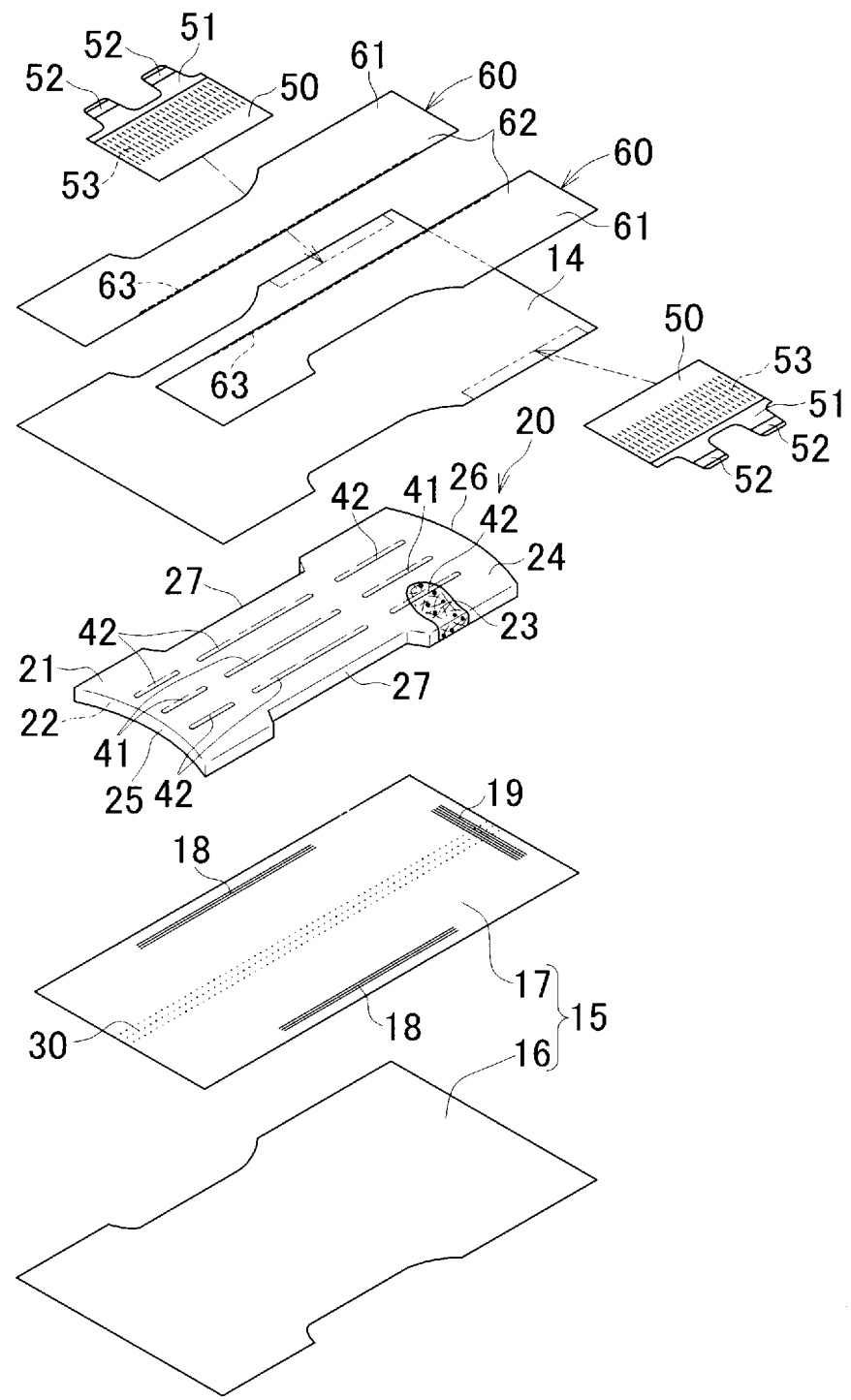
FIG. 3 is an exploded perspective view of the diaper according to FIG. 1.
Figure 4:
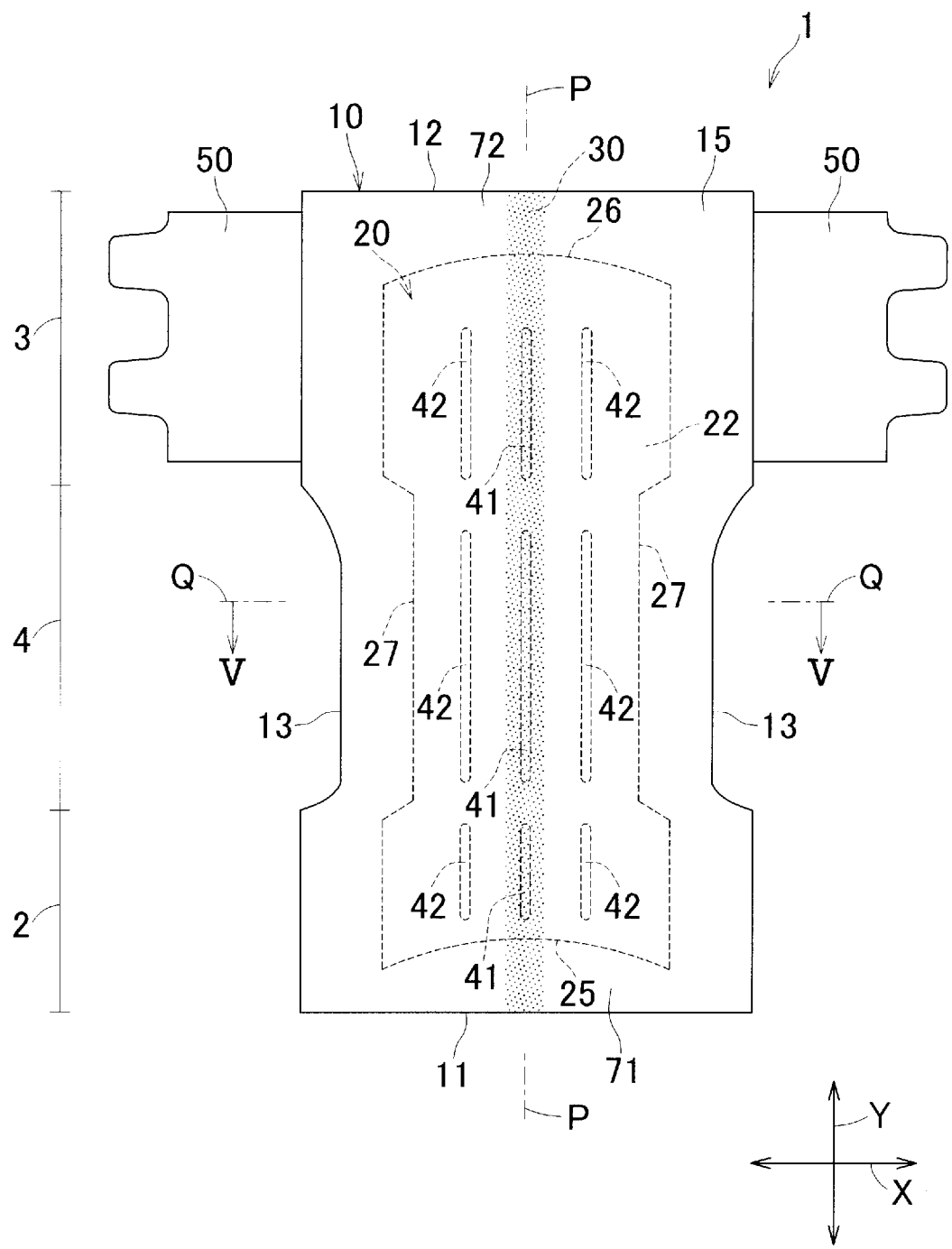
FIG. 4 is a developed plan view of the diaper according to FIG. 1 as viewed from its garment-facing side.
Figure 5:
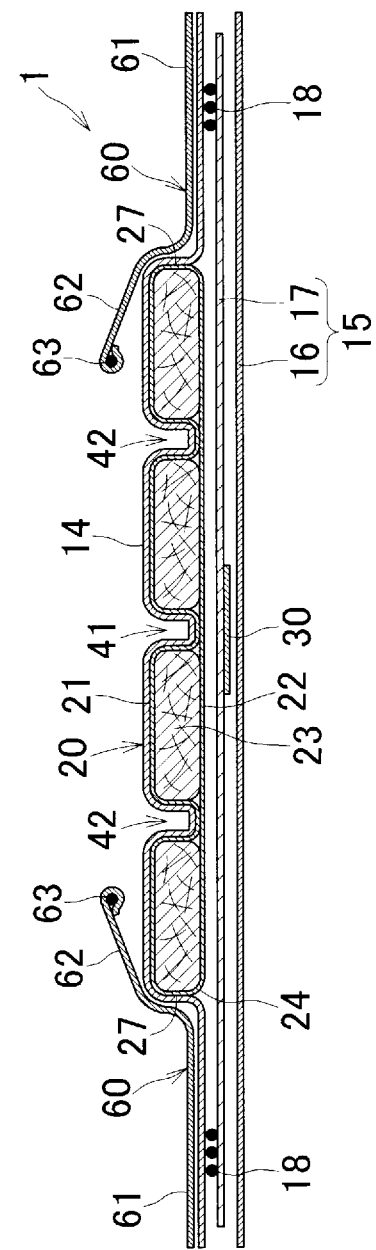
FIG. 5 is a sectional view of the diaper according to FIG. 1 taken along line V-V in FIG. 4.

In the diaper 1 according to the present embodiment, the display area 30 can be visually recognized from the garment-facing side through the first outer sheet 16 as will be apparent from FIGS. 1 and 4 and from the wearer's body-side, also through the central void 41 of the liquid-absorbent structure as will be apparent from FIG. 2. The first outer sheet 16 has a total luminous transmittance of about 20 to about 90%, preferably of about 70 to about 85% and specifically of about 82% in the present embodiment. With this total luminous transmittance, the display area 30 can be visually recognized through the first outer sheet 16. The display area 30 can be visually recognized not only from the garment-facing side but also from the skin-facing side in the central void 41 through the second outer sheet 17, the wrapping sheet 24 and the inner sheet 14 since the display area 30 is formed on the outer surface of the second outer sheet 17. In order that the display area 30 can be visually recognized through these sheets, it is required for these sheets to have a total luminous transmittance of about 20 to about 90%, preferably of about 30 to about 80% and specifically of about 32% in the present embodiment.

The total luminous transmittance was measured according to JIS-K7105. For this measurement, flicker photometer-type colorimeter Z-300A (Nippon Denshoku Industries Co., Ltd.) was used. More specifically, the inventors prepared samples each having a width dimension of 30 mm and a length dimension of 30 mm from the portion of the diaper 1 including the first outer sheet 16 and the central void 41 to conduct the measurement of total luminous transmittance. For each of these samples, the first and second outer sheets 16, 17 bonded to each other via hot melt adhesives was subjected to cold spray at a temperature of −40° C. to reduce the bonding effect of hot melt adhesives and the first outer sheet 16 was peeled off from the second outer sheet 17 before the measurement.

In the diaper 1 according to the present embodiment, at least the central void 41 positioned over the display area 30 is formed intermittently in the longitudinal direction Y to define three segments spaced one from another so that the display area 30 can be partially recognized. In other words, the display area 30 cannot be visually recognized from the skin-facing side between each pair of the adjacent segments of the central void 41. The display area 30 adapted to be visually recognized from the garment-facing side can be visually recognized from the skin-facing side also at least through the central void 41 and therefore it is not required to form the display area 30 on both the garment-facing side and the skin-facing side, respectively. While the central void 41 is formed of three segments spaced one from another in the longitudinal direction Y in the present embodiment, it is possible to form the central void 41 by a single segment continuously extending in the longitudinal direction Y or to enlarge a length of the central void 41 in the longitudinal direction Y. However, a quantity of the core material will be correspondingly reduced and, in consequence, there is a possibility that its liquid absorption capacity might be reduced. Therefore, the length dimension of the central void 41 in the longitudinal direction Y and the distance between each pair of the adjacent segments of the central void 41 are preferably determined in consideration of an appropriate compatibility between the absorption capacity of the core 23 and the visibility of the display area 30.

The display area 30 can be visually recognized from the skin-facing side also through the front and rear flaps 71, 72. Specifically, the front and rear flaps 71, 72 are respectively formed exclusively by the inner and outer sheets 14, 15 laminated together so that the display area 30 may be visually recognized through these inner and outer sheets 14, 17. This means that a center position of the diaper 1 can be confirmed on the front and rear ends of the diaper 1 and the diaper 1 can be properly positioned with respect to the wearer's body in the course of putting the diaper 1 on the wearer's body. Specifically, the display area 30 visually recognized through the rear flap 72 may be aligned with the wearer's backbone and the display area 30 visually recognized through the front flap 71 may be aligned with the wearer's bellybutton to position the diaper 1 on the wearer's body. Even if the diaper 1 is displaced in the transverse direction X after the diaper 1 has been put on the wearer's body, the display area 30 may be realigned with the wearer's backbone and/or bellybutton to correct such displacement of the diaper 1.

The diaper 1 as has been described above is useful also when the diaper 1 is used in combination with a separately prepared so-called urine absorbing pad usually dimensioned to be smaller than the diaper 1 and placed on the skin-facing side of the diaper 1. With such pad placed on the diaper 1, the central void 41 is covered with the pad and the central void 41 might be hindered from being visually recognized. Even in such situation, the display area 30 can be visually recognized through the front and rear flaps 71, 72 and the diaper 1 can be properly put on the wearer's body using the portions of the display area 30 visually recognized through the front and rear flaps 71, 72 so that the pad may be centered with respect to the diaper 1. When the diaper 1 is inserted between the dorsal side of the wearer lying face up and the bed or the floor, the central void 41 might be hidden from view. Even in such situation, the display area 30 can be visually recognized at least through the front and rear flaps 71, 72. Such feature is effective particularly in the case of the diaper 1 for adult because the central void 41 may often be hidden from view under the wearer's relatively big body.

The diaper 1 for adult may be put on the wearer's body particular when the wearer is a bedridden person by following procedural steps as will described below. Considering that the wearer is adult and therefore relatively weighty, a helper may place the wearer on his or her one side, lay the diaper 1 on the position selected to face the wearer' buttock and then turn the wearer's body upward to lie face up again with his or her buttock placed on the diaper 1. In the course of putting the diaper 1 on the wearer's body in this manner, the display area 30 can be visually recognized from the inner side of the diaper 1 and this may be utilized to position the diaper 1. When it is found that the diaper 1 is unacceptably displaced from the proper position, the helper may turn the wearer's body onto the other side and position the diaper 1 again. Conventionally, in the course of turning the wearer's body once or twice for positioning of the diaper 1, it might become impossible to confirm the center line of the diaper 1. However, the display area 30 adapted to be visually recognized from the inner side of the diaper 1 assures to overcome such problem and to position the diaper 1 properly with respect to the wearer's body. In this manner, the diaper 1 according to the present invention is suitable particular for the bedridden adult person.

With the arrangement such that the display area 30 appears to be continuous in the longitudinal direction as viewed from the garment-facing side and appears to be discontinuous at the front and rear ends 11, 12 and in the central void 51, this facilitates the inner and outer surfaces to be distinguished from each other and prevents these both surfaces from being inside out with the diaper 1 is put on the wearer's body. The diaper 1 according to the present embodiment is of so-called open-type and the hook elements 52 may be engaged with the garment-facing side of the outer sheet 15 in the front waist region 2 to obtain the diaper 1 shown by FIG. 1. When the hook elements 52 are engaged with the outer sheet 15, the display area 30 formed to extend along the imaginary longitudinal center line P-P may be utilized to achieve laterally even engagement. If the engagement is not laterally even, one of the leg-openings will be relatively small and the other of the leg-openings will be relatively large. As a result, the peripheral edge of the smaller leg-opening will come in excessively tight contact with the associated leg of the wearer and the peripheral edge of the larger leg-opening will come in unacceptably loose contact with the associated leg of the wearer leaving a gap between the leg and the peripheral edge. Eventually it will be apprehended that body waste such as urine might leak out through such gap. The display area 30 can effectively eliminate such apprehension.

The central void 41 is formed along the imaginary longitudinal center line P-P and can be visually recognized from the skin-facing side. This central void 41 visually recognized from the skin-facing side may be aligned with the bottom cleavage of the wearer to center the diaper 1 with respect to the wearer's body. More specifically, when the rear waist region 3 may be placed on the wearer' dorsal region and the front waist region 2 may be placed on the wearer' ventral region to cover the wearer's crotch with the crotch region 4, the display area 30 in the rear flap 72 is prevented by the wearer's dorsal region from being visually recognized. However, the display area 30 can be visually recognized at least through the central void 41 in the crotch region 4 and the front waist region 2 and this sub-region of the display area 30 may be aligned with a central sub-region and the bellybutton of the wearer in the course of putting the diaper 1 on the wearer's body to position the diaper 1 in proper relation with the wearer's body. If the display area 30 can be visually recognized through the central void 41 in the rear waist region in the course of putting the diaper 1 on the wearer's body, it is also possible to put the diaper 1 on the wearer's body by such visually recognizable segment of the display area 30 by aligning this segment with the wearer's bottom cleavage.

The liquid-absorbent structure 20 is formed with the central void 41 extending in the longitudinal direction Y and the lateral voids 42 and, in consequence, stiffness in these voids 41, 42 is inevitably reduced. Such differential stiffness facilitates the liquid-absorbent structure 20 to be folded along the central void 41 and the lateral voids 42 so that the liquid-absorbent structure 20 as a whole may be smoothly bowed and come in close contact with the wearer's body. Consequently, body waste such as urine can be quickly absorbed and thereby leakage of body waste such as urine can be effectively prevented.

The central void 41 and the lateral voids 42 may be formed, for example, by a method as follows. A mold used to form the core 23 is formed in regions thereof corresponding to the voids 41, 42 with protuberances so that none of the core materials may be laminated in these regions and the voids 41, 42 in which substantially none of the core materials is present may be formed. Alternatively, from a core 23 over the entire area of which the core materials are laminated in substantially uniform manner, the core material may be cut out by a hand chaff cutter at respective regions of the core 23 corresponding to the voids 41, 42 to form these voids 41, 42.

While the display area 30 is formed on the outer surface of the second outer sheet 17 according to the present embodiment, it is possible to form the display area 30 on the inner surface of the second outer sheet or on the inner or outer surface of the first outer sheet 16. However, considering undesirable color migration to the wearer's garment, it is desired to form the display area 30 on the surface free from possibility that the display area 30 might come in direct contact with the wearer's garment. As the display area 30, in addition to various types of print, an indicator exhibiting color reaction in response to contact with moisture of bodily fluids may be used. Use of such indicator allows occurrence of urination to be detected. The display area 30 can be visually recognized from both of the skin-facing side and garment-facing side of the diaper 1. In consequence, any change in color appearing on the indicator also can be recognized from both of the skin-facing side and garment-facing side of the diaper 1. The diaper 1 provided with such indicator is particularly effective as the diaper 1 for bedridden adult. Specifically, when the wearer is a bedridden adult, it is easier and more convenient to observe the display area 30 from the outer side of the diaper 1 after one of the hook elements 52 of the diaper 1 has been temporally disengaged for inspection, than to observe the display area 30 from the outer side of the diaper 1. This is for the reason that, if any change of color in the indicator visually recognized from the inner side of the worn diaper 1, the diaper 1 may be immediately exchanged with a fresh one.

A length dimension of the display area 30 in the transverse direction X (i.e. its width) is larger than a length dimension in the corresponding direction X of the central void 41 positioned over the display area 30. Specifically, in a preferred embodiment, the length dimension of the display area 30 in the transverse direction X (i.e. its width) is about 20 to about 100 mm and that of the central void 41 is about 5 to about 20 mm. With such dimensional relation between the display area 30 and the central void 41, even if a position at which the liquid-absorbent structure 20 is placed on or within the chassis 10 is displaced with respect to the chassis 10 in the transverse direction X, the liquid-absorbent structure 20 can overlap the display area 30. The display area 30 may be formed in one of the front and rear waist regions 2, 3 and the central void 41 and/or the lateral voids 42 may be positioned over the display area 30. The central void 41 and the lateral voids 42 may be defined by the slits extending in the longitudinal direction Y or by dots arranged intermittently and spaced one from another in the longitudinal direction Y. In any case, the diaper 1 may include the region in which the display area 30 can be visually recognized from the skin-facing side.

In the diaper 1 having been described above, regions in which the display area 30 and the central void 41 coincide with each other may be pressed in the thickness direction thereof, so putting the wrapping sheet 24 lying on the first surface 21 and the second surface 22 in close contact with the inner sheet 14. In this way, degradation of total luminous transmittance, in consequence, degradation of visibility of the display area 30 can be prevented. Furthermore, the sections of the wrapping sheet 24 lying on the first surface 21 and the second surface 22 may be bonded together in the voids 41, 42 to restrict displacement of the core materials in the transverse direction X and thereby to assure a shape retention of the core 23. Press working may be carried out, for example, by introducing a stack of the chassis and the liquid-absorbent structure 20 in a nip defined between an annular pressure roll, at least having a width dimensioned to cover the central void 41, and an anvil roll. As the pressure roll, it is possible to use a pressure roll formed with protuberances in the region at least corresponding to the central void 41.

The central void 41 is the area in which the core 23 is substantially not present and, in this area, the wrapping sheet 24 may be bonded to itself to form a depression which is concave in the thickness direction from the first surface 21 and the second surface 22. The depression formed in this manner allows this area adapted to be visually and tactually recognized. The display area 30 can be visually recognized through the central void and the depression formed in this manner further facilitate this display area to be recognized.

The core 23 and the wrapping sheet 24, the wrapping sheet 24 and the inner sheet 14, and the wrapping sheet 24 and the second sheet 17 are respectively bonded to each other by hot melt adhesives or the like. Such bonding treatment is preferably carried out by using materials or techniques selected to be free from apprehension that the total luminous transmittance might be degraded due to the bonding means. For example, the respective sheets may be coated with hot melt adhesive applied in an omega-pattern or a spiral pattern.

While the display area 30 can be distinguished from the inner and outer sheets 14, 15 by the differential color phase according to the present embodiment, it is possible to distinguish the display area 30 from the inner and outer sheets 14, 15 by differentiated color saturation or color brightness. While the display area 30 is formed of a continuous straight line according to the present embodiment, it is possible to form the display area 30 by a curved line or dots arranged intermittently in the longitudinal direction Y or by a combination thereof. Furthermore it is also possible to form the display area 30 by letters or graphics such as a corporate mark.

In the diaper 1 as has been described above, it is also possible, for example, to sandwich a liquid-impervious leakage-barrier sheet between the liquid-absorbent structure 20 and the second outer sheet 17 or to sandwich a liquid-pervious second sheet between the inner sheet 14 and the liquid-absorbent structure 20. Even when the additional sheets are laminated in this manner, the display area 30 can be visually recognized from the skin-facing side though these sheets so far as the total luminous transmittance of these sheets is maintained at about 20 to about 90%.

While the chassis 10 has been described to comprise the inner and outer sheets 14, 15, the invention is not limited to such construction. For example, the chassis 10 may be defined by a single sheet or may include other sheet or sheets. While the liquid-absorbent structure 20 is sandwiched between the inner and outer sheets 14, 15 according to the present embodiment, the position at which the liquid-absorbent structure 20 is provided may be appropriately changed depending on the construction or other factors of the chassis 10.

<Second Embodiment>

Figure 6:
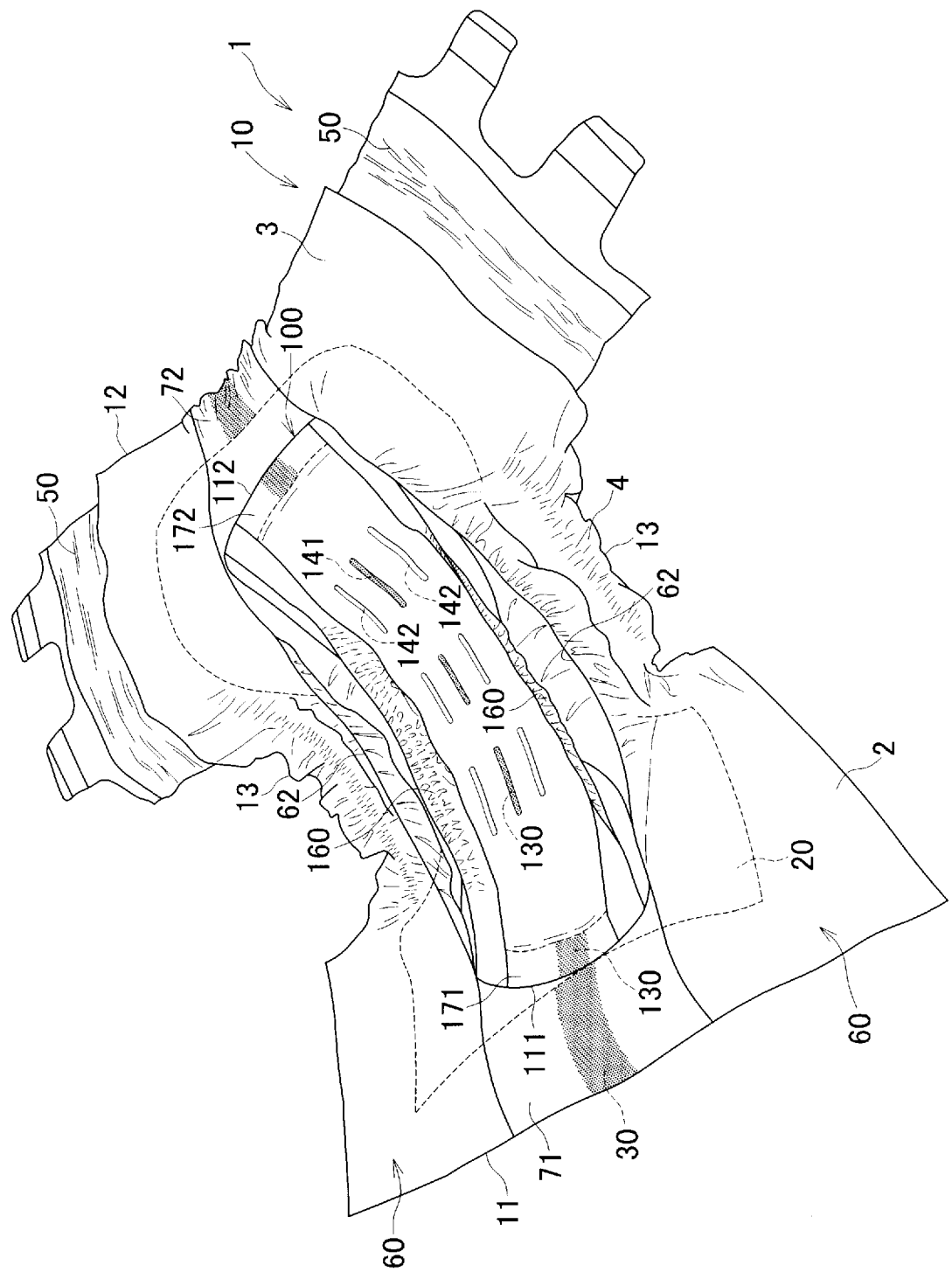
FIG. 6 is a perspective view of a diaper-pad assembly according to a second embodiment of the present invention.
Figure 7:
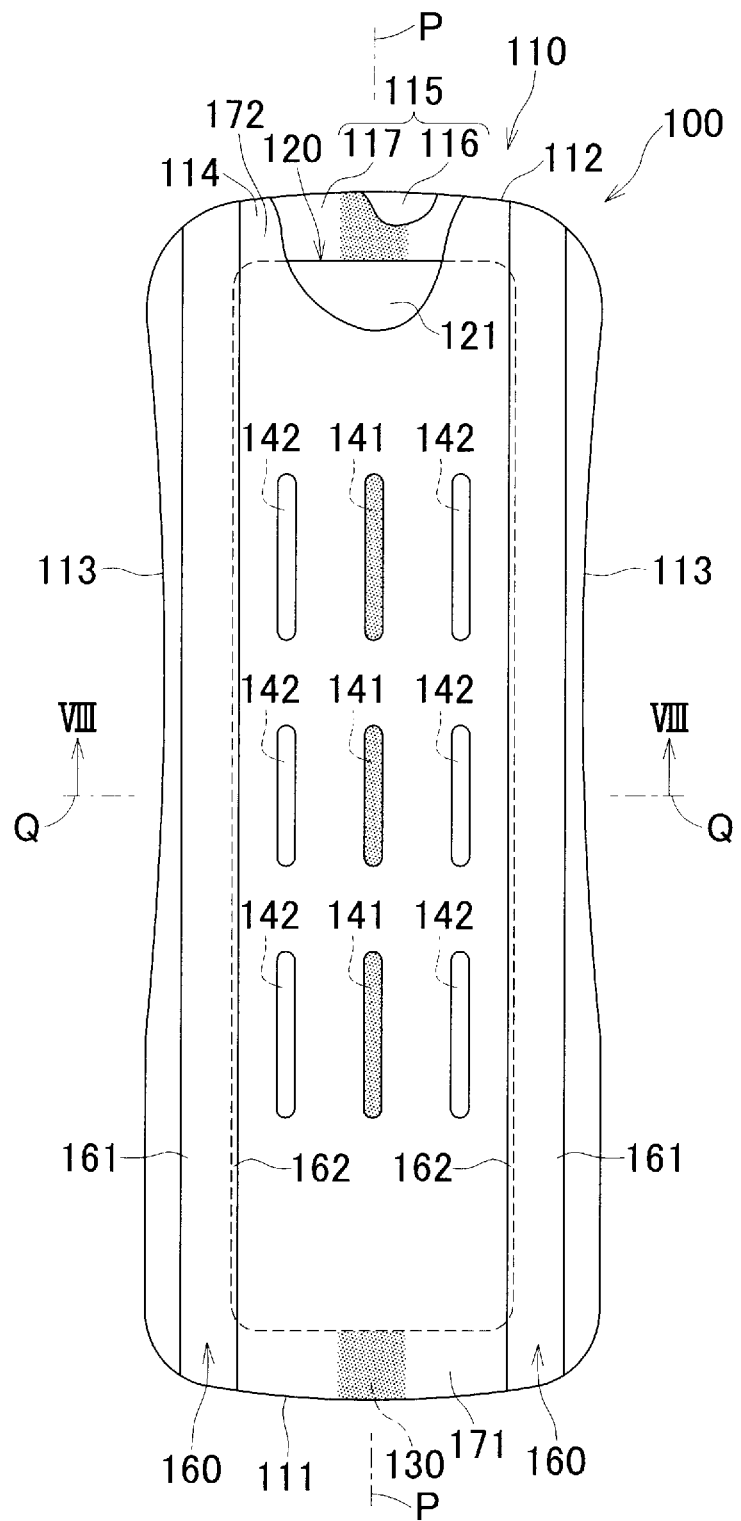
FIG. 7 is a plan view of the pad as viewed from the skin-facing side.
Figure 8:
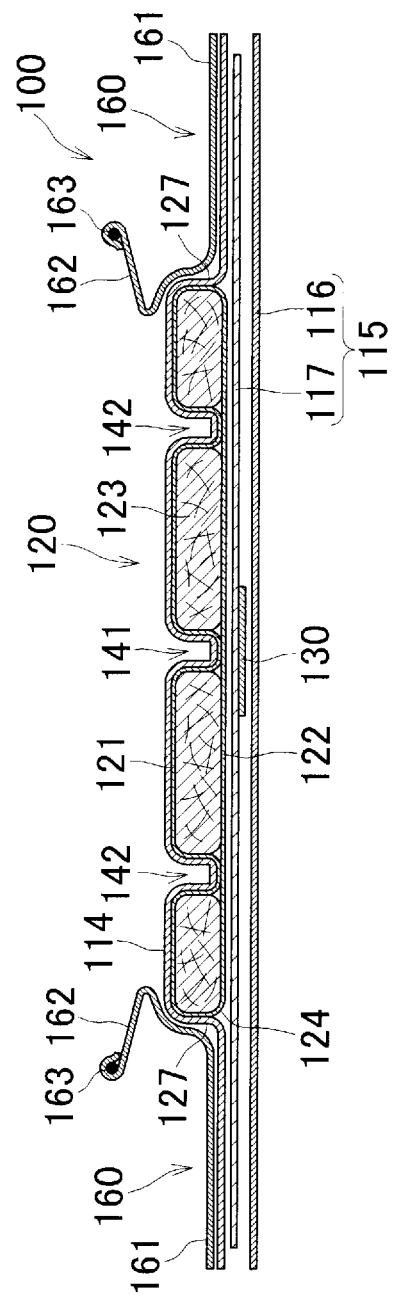
FIG. 8 is a sectional view of the diaper-pad assembly according to FIG. 6 taken along line VIII-VIII in FIG. 7.

FIGS. 6 through 8 illustrate a second embodiment of the present invention. According to this second embodiment, as will be apparent from FIG. 6, the diaper 1 (first independent article) is used in combination with the disposable pad 100 (second independent article) to form an absorbent article. The diaper 1 itself is similar to the diaper 1 according to the first embodiment and details will not be repetitively described hereunder.

The pad 100 has a construction substantially similar to the diaper 1 except that the pad 100 is not provided with side flap sheets and dimensioned to be smaller than the diaper 1 in the longitudinal direction Y as well as in the transverse direction X. Components of the pad 100 similar to those of the diaper 1 are designated with the reference numerals similar to those in the diaper 1 and details of these similar components will not be repetitively described hereunder. The components similar to those in the diaper 1 are designated by the reference numerals represented by 100 plus the reference numbers used for the corresponding components in the first embodiment to distinguish from them.

The pad 100 comprises a chassis 110, a liquid-absorbent structure 120 and optional leakage-barrier cuffs 160. The chassis 110 comprises a liquid-pervious inner sheet 114, a liquid-impervious outer sheet 115 wherein the outer sheet 115 comprises, in turn, a first outer sheet 116 lying on the garment-facing side and a second outer sheet 117 lying on the inner side of the first outer sheet 116. Between the inner and outer sheets 114, 115, the liquid-absorbent structure 120 is sandwiched and the liquid-absorbent structure 120 has a first surface 121, a second surface 122 opposite to the first surface 121, a liquid-absorbent core 123 and a wrapping sheet 124 adapted to wrap the core 123. Leakage-barrier cuffs 160 are attached to the skin-facing side of the inner sheet 114. The leakage-barrier cuffs 160 are spaced from each other in the transverse direction X and extend in the longitudinal direction Y and respectively have outer side edges 161 bonded to the inner sheet 114 and inner side edges 162 not bonded to the inner sheet 114. The respective inner side edges 162 are provided with a plurality of barrier cuff elastic elements 163 attached thereto under tension in the longitudinal direction Y and in a contractible manner.

Referring to FIG. 6, length dimensions of the pad 100 in the longitudinal direction X as well as in the transverse direction Y are smaller than those of the diaper 1. Consequently, front and rear ends 111, 112 of the chassis 110 lie inboard of the front and rear ends 11, 12 of the chassis 10 in the diaper 1 as viewed in the longitudinal direction Y and side edges 113 of the chassis 110 in the pad 100 lie inboard of the side edges 13 of the chassis 10 in the diaper 1 as viewed in the transverse direction X. The pad 100 as a whole lies inboard of the leakage-barrier cuffs 60 of the diaper 1 as viewed in the transverse direction X.

The pad 100 is formed on the surface of the second outer sheet 117 facing the first outer sheet 116 with a display area 130. The display area 130 continuously extends in the longitudinal direction Y to the front and rear ends 111, 112 of the chassis 110 and extends outward from front and rear ends 125, 126 of the core 123 to define front and rear flaps 171, 172. This display area 130 can be visually recognized through the first outer sheet 116.

The display area 130 can be visually recognized from the skin-facing side also through a central void 141. Furthermore, the display area 130 can be visually recognized from the skin-facing side also through the front and rear flaps 171, 172.

When the diaper 1 is used in combination with such pad 100 placed on the inner side of the diaper 1, the display area 130 extending along the imaginary longitudinal center line P-P can be visually recognized from the skin-facing side through the central void 141 and the front and rear flaps 171, 172. The display area 130 visually recognized in this manner may be utilized as a reference line to align the center line of the pad 100 with the center line of the diaper 1. In other words, the display area 30 of the diaper 1 can be aligned with the display area 130 of the pad 100 as viewed in the longitudinal direction Y. The pad 100 may be attached to the diaper 1 in this manner to prevent the pad 100 and the diaper 1 being displaced from each other in the transverse direction X.

The segment of the display area 130 visually recognized through the central void 141 of the pad 100 and the segments visually recognized of the display area 130 through the front and rear flaps 171, 172 may be aligned with the wearer's bottom cleavage, crotch center and bellybutton to center the pad 100 to the wearer's body. The diaper 1 combined with such pad 100 is often used in such a manner in which only the pad 100 soiled with body waste is exchanged with a fresh pad and the diaper 1 is reused. In such case also, the display area 130 facilitates the pad 100 to be aligned not only with the diaper 1 but also with the wearer's body.

In the absorbent article having been described above, the display area 30 of the diaper 1 appears on the inner side of the diaper 1. At least the display area 30 of the diaper 1 may be provided in the form of an indicator adapted to be changed in color when it is wetted with body waste such as urine to confirm that body waste such as urine has reached the diaper 1. If it is confirmed that body waste such as urine has reached the diaper 1, the diaper 1 also may be exchanged with a fresh one. In other words, by providing the display area 30 of the diaper 1 in the form of the indicator, it can be determined whether not only the pad 100 but also the diaper 1 must be exchanged with a fresh diaper 1.

The pad 100 is positioned inboard of the leakage-barrier cuffs 60 of the diaper 1 as viewed in the transverse direction X and thereby the pad 100 is prevented by the leakage-barrier cuffs 60 from being displaced in the transverse direction X. Not only the diaper 1 but also the pad 100 is formed with the leakage-barrier cuffs 160 to prevent, further and reliably, body waste such as urine from leaking out.

The component members of the diaper 1 and the pad 100 are not limited to those described in the present specification and other various types of material widely used in the related technical field may be used. While the open-type diaper 1 has been exemplarily described above, the present invention is applicable to so-called pull-on type diaper in which opposite side edges of the front and rear waist regions 2, 3 have previously been joined together. In the course of stacking the pad 100 on the diaper 1 in the thickness direction thereof, it is possible to stack further additional pad as an independent article on the former pad 100 so as to lie on the side directly facing the wearer's body.

<Third Embodiment>

Figure 9:
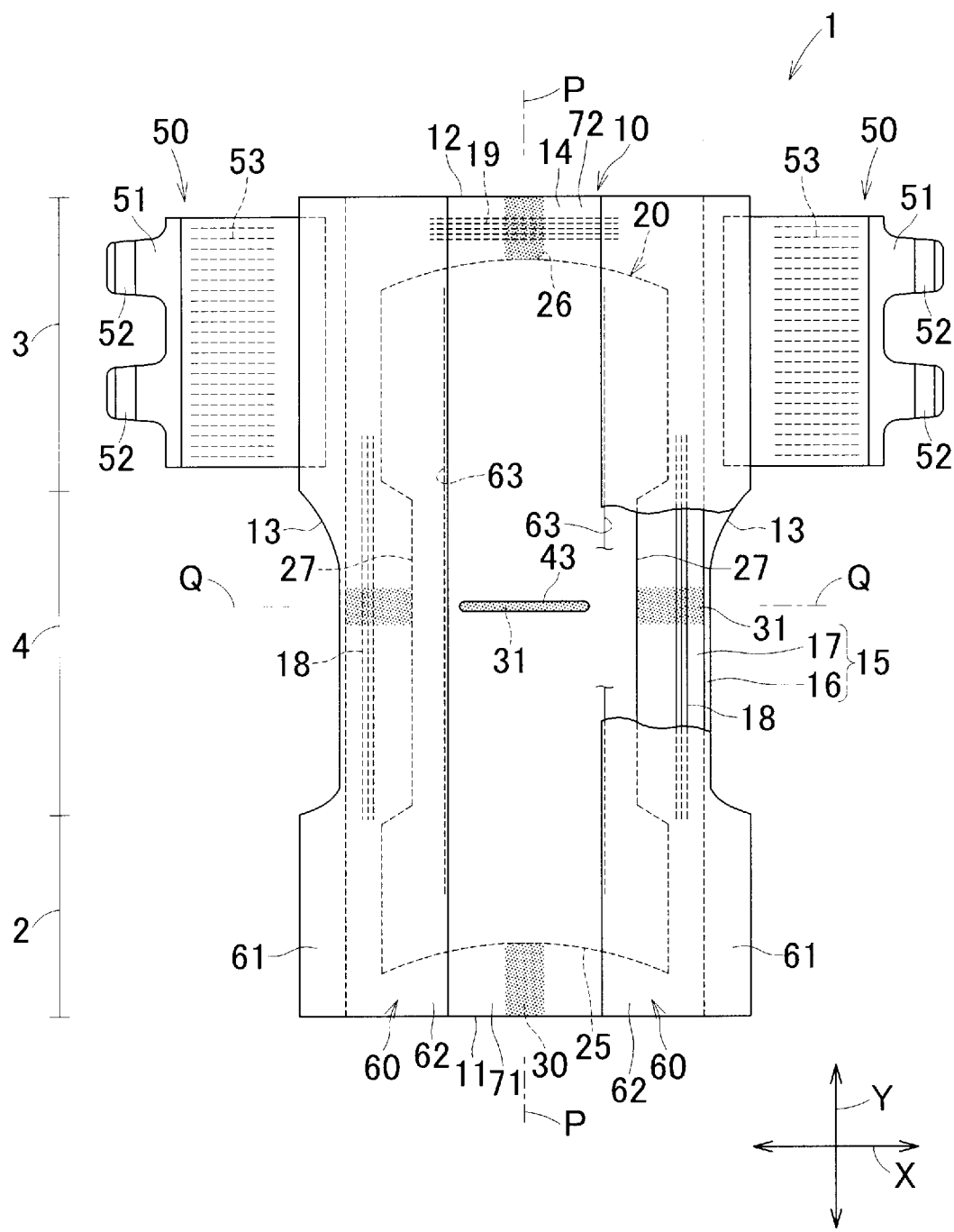
FIG. 9 is a view similar to FIG. 2, showing a diaper according to a third embodiment of the present invention.
Figure 10:
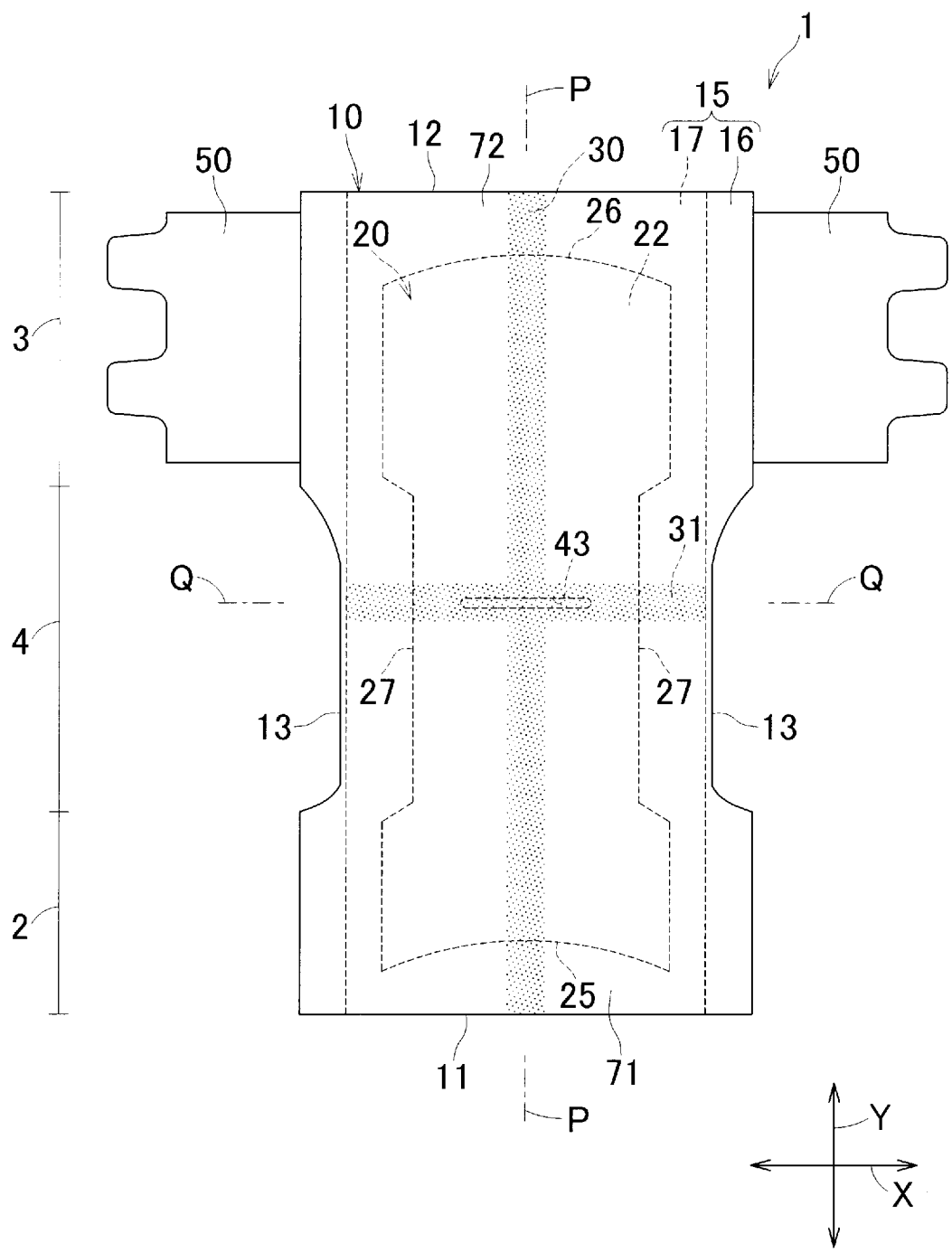
FIG. 10 is a view similar to FIG. 4, showing a diaper according to the third embodiment of the present invention.

FIGS. 9 and 10 illustrate a third embodiment of the present invention wherein FIG. 9 is a partially cutaway view similar to FIG. 2 and FIG. 10 is a view similar to FIG. 4. The present embodiment includes, in addition to the display area 30 extending in the longitudinal direction Y, a display area 31 extending in the transverse direction and an elongate void 43 positioned over the display area 31. The third embodiment is similar to the first embodiment except for this feature. The components similar to those of the first embodiment will be designated by the same reference numerals as those in the first embodiment and details thereof will not be repetitively described hereunder.

A display area 31 extends between the opposite side edges 13 of the chassis 10 in the transverse direction X along the imaginary transverse center line Q-Q. In this way, the display area 30 and the display area 31 intersect substantially at a right angle. These display areas 30, 31 are formed on the side of the second outer sheet 17 facing the liquid-absorbent structure 20 and can be visually recognized from the garment-facing side through the first outer sheet 16.

The liquid-absorbent structure 20 is formed with the void 43 extending in the transverse direction X. The void 43 is a slit-like segment extending along the imaginary transverse center line Q-Q and positioned over the display area 31. The presence of the void 43 allows the display area 31 to be visually recognized from the skin-facing side of the diaper 1. Specifically, the display area 31 can be visually recognized through the wrapping sheet 24 and the inner sheet 14. The display area 31 adapted to be visually recognized makes it possible for the helper, when it is desired to put the diaper 1 on the wearer's body, to confirm the display area 31 as the bisector of the length dimension of the diaper 1 in the longitudinal direction Y corresponding to the imaginary transverse center line Q-Q and to align it with the center line of the wearer's body. Specifically, the display area 31 partially overlaps the imaginary transverse center line Q-Q and may be positioned in the wearer's crotch region to prevent the diaper 1 from being displaced toward the ventral side or the dorsal side of the wearer.

While the display area 31 fully extends between the opposite side edges 13 of the chassis 10 in the transverse direction X according to the present embodiment, it is also possible to form the display area extending only over a part of the width of the chassis 10. However, the display area 31 fully extending between the opposite side edges 13 of the chassis 10 extends outward beyond the side edges of the liquid-absorbent structure 20 in the transverse direction X and allows the display area 31 to be visually recognized. In this case, the display area 31 can be visually recognized outside the liquid-absorbent structure 20 as viewed in the transverse direction X through the inner sheet 14 and the leakage-barrier cuffs 60. According to this embodiment, as will be apparent from FIG. 9, the display area 31 can be visually recognized outboard of the liquid-absorbent structure 20 in the transverse direction X through the inner sheet 14 and the leakage-barrier cuffs 60 so far as the inner sheet 14 and the leakage-barrier cuffs 60 are in close contact one with another. Upon contraction of the barrier cuff elastic elements 63, the leakage-barrier cuffs 60 are spaced upward from the inner sheet 14 and it is no more possible to visually recognize the display area 31 through the inner sheet 14 and the leakage-barrier cuffs 60. In this case, the display area 31 can be visually recognized through a gap defined between the inner sheet 14 and the leakage-barrier cuffs 60. In a region where the inner sheet 14 and the leakage-barrier cuffs 60 are bonded together, the display area 31 can be visually recognized from the skin-facing side even if the leakage-barrier cuffs 60 are spaced upward from the inner sheet 14.

While the void 43 is provided in the form of the slit-like segment according to the present embodiment, it is also possible to form this void 43 in another fashion, for example, intermittent slit-like segments. The void 43 in the form of a continuous slit-like segment or intermittent slit-like segment advantageously facilitates the diaper 1 to be folded along this void 43 and to be compactly rolled up. In this way, the diaper 1 would not become bulky for storage. Furthermore, with the diaper 1 put on the wearer's body, the continuous slit-like void 41 makes it possible to form a pocket adapted for temporary retention of body waste such as urine and thereby to prevent urine leakage.

It is also possible to find additional void(s) positioned over the display area 30 extending in the longitudinal direction Y. The void positioned over the display area 30 and the void positioned over the display area 31 may be combined with each other to prevent concurrently the diaper 1 from being displaced in the transverse direction X and in the longitudinal direction Y. It should be noted here that the display area 30 extending in the longitudinal direction Y is not the essential feature and may be eliminated in this embodiment.

The term "first" and "second" used in the specification and claims of the present invention are used merely to distinguish the similar elements, similar positions or the other similar means. In the specification and claims of the present invention the term "first waist region" means one of the front and rear waist regions and the term "second waist region" means the other of the front and rear waist regions.

The first aspects of the present invention described above may be arranged in at least the following items:

(i) A disposable absorbent article comprising:
a chassis having a longitudinal direction, a transverse direction, a skin-facing side and a garment-facing side; and
a liquid-absorbent structure containing therein an absorbent core and positioned on or within the chassis; wherein the chassis is formed with a display area which overlaps with the liquid-absorbent structure and is adapted to be visually recognized from the garment-facing side; and wherein
the liquid-absorbent structure is formed with at least one void therethrough in which the core is substantially absent, the void being positioned over the display area so that the display area may be visually recognized from the skin-facing side through the void.

One or more aspects of the present invention described in the above item (i) may provide one or more of the following advantageous effects:

(a) the liquid-absorbent structure is formed with the void in which the core is substantially absent so that the display area may be visually recognized from the side facing the wearer's body through this void. With such unique arrangement, the display area can be visually recognized from both the skin-facing side and the garment-facing side without forming both the skin-facing side and the garment-facing side of the absorbent article with respective display areas.

Additionally, one or more of the following embodiments are provided in accordance with further aspects:

(ii) The chassis comprises a first waist region corresponding to either a front or rear waist region, a second waist region corresponding to the other of the front or rear waist region and a crotch region extending between the first and second waist regions;
the liquid-absorbent structure extends along the crotch region into the first and second waist regions; and
the void is formed at least in one of the first and second waist regions.

(iii) A region in which the void and the display area coincide with each other, this region being closer to the skin-facing side of the article than the display area, exhibits a total luminous transmittance at 20 to 90%.

(iv) The chassis is contoured by front and rear ends extending in the transverse direction and opposite side edges extending in the longitudinal direction and the display area continuously extends from the front end of the chassis to the rear end of the chassis in the longitudinal direction;
the core is contoured by front and rear ends extending in the transverse direction and a pair of opposite side edges extending in the longitudinal direction; and front and rear flaps are defined between the front and rear ends of the core and the front and rear ends of the chassis so that the display area may be visually recognized from the skin-facing side through the front and rear flaps.

(v) The void is formed to extend either in the longitudinal direction or in the transverse direction.

(vi) The void comprises at least one elongate void extending in the longitudinal direction or at least one elongate void extending in the transverse direction.

(vii) A plurality of the voids are formed to be spaced one from another in the longitudinal direction.

(viii) The liquid-absorbent structure includes a sheet laminated on the surface of the core lying on the skin-facing side and a sheet laminated on the surface of the core lying on the garment-facing side and these two sheets are bonded to each other in the void.

(ix) The display area develops a color reaction upon contact with at least one of moisture and bodily fluids.

(x) The second waist region is formed with engagement means adapted to be engaged with the first waist region.

(xi) The disposable absorbent article, further comprising: a composite of a plurality of the disposable absorbent articles which are each different in size and are stacked in the thickness direction, wherein the disposable absorbent article having the largest length dimension is positioned closest to the garment-facing side of the composite disposable absorbent article and the disposable absorbent article having the smallest length dimension is positioned closest to the skin-facing side of the composite disposable absorbent article and any disposable absorbent articles stacked in between are sized in order of length dimension such that, in the composite disposable absorbent article, the lengths of the stacked disposable absorbent articles decrease from the garment-facing side to the skin-facing side in the longitudinal direction.

(xii) The display area extends in a longitudinal direction.

(xiii) The display area extends the full length of the chassis.

(xiv) The display area continuously and rectilinearly extends in the longitudinal direction.

(xv) The void and the display area coincide with each other exhibits a total luminous transmittance at 30 to 80%.

(xvi) The display area extends along at least one of a longitudinal center line and a transverse center line of the chassis.

(xvii) The chassis comprises an inner sheet lying on a skin-facing side and an outer sheet lying on a garment-facing side, and wherein the liquid-absorbent structure is sandwiched in between the inner and outer sheets of the chassis.

(xviii) The outer sheet of the chassis comprises a first outer sheet and a second outer sheet lying on the skin-facing side of the first outer sheet, and wherein the second outer sheet is formed on its garment-facing side with the display area.

(xix) The void comprises at least one central void extending along a longitudinal center line of the article and lateral voids formed in parallel thereto on either side of the central void or voids.

(xx) The lateral voids are not positioned over the display area.

(xxi) The void is one of slit-shaped and dot-shaped.

(xxii) The width of the display area is larger than the width of the void positioned thereover.

(xxiii) The display area has a width of about 20 to about 100 mm and the void has a width of about 5 to about 20 mm.

According to the embodiments in the above (ii) to (xxiii), the features of which may be taken in isolation or in combination with one another, the advantageous effect(s) set forth at (a) is/are better ensured. Further advantageous effects of the respective embodiments may be obtained as discussed in the respective related descriptions.

The invention claimed is:

1. A disposable absorbent article, comprising:
    a chassis having a longitudinal direction, a transverse direction, a thickness direction, a skin-facing side and a garment-facing side, the chassis being contoured by front and rear ends extending in the transverse direction and opposite side edges extending in the longitudinal direction;
    a liquid-absorbent structure including an absorbent core and positioned on or within the chassis, the absorbent core being contoured by front and rear ends extending in the transverse direction and a pair of opposite side edges extending in the longitudinal direction; and
    front and rear flaps between the front and rear ends of the core and the front and rear ends of the chassis,
    wherein
    the chassis is formed with a display area which overlaps the liquid-absorbent structure and which is visually recognizable from the garment-facing side,
    the display area continuously extends from the front end of the chassis to the rear end of the chassis in the longitudinal direction, and is spaced apart from the opposite side edges of the chassis,
    the liquid-absorbent structure is formed therethrough with at least one void in which the core is substantially absent, the void being positioned over the display area so that the display area is visually recognizable from the skin-facing side through the void,
    an entirety of the display area has a different color from a remainder of the chassis and is visually recognizable from the skin-facing side through the front and rear flaps,
    the liquid-absorbent structure further includes
        a first surface laminated on a surface of the core lying on the skin-facing side; and
        a second surface laminated on a surface of the core lying on the garment-facing side, and
    the first and second surfaces are directly bonded to each other in the void.

2. The disposable absorbent article defined by claim 1, wherein
    the chassis comprises a first waist region corresponding to either a front or rear waist region, a second waist region corresponding to the other of the front or rear waist region, and a crotch region extending between the first and second waist regions;
    the liquid-absorbent structure extends along the crotch region into the first and second waist regions; and
    the void is formed at least in one of the first and second waist regions.

3. The disposable absorbent article defined by claim 1, wherein a region in which the void and the display area coincide with each other, this region being closer to the skin-facing side of the article than the display area, exhibits a total luminous transmittance in a range of 20 to 90%.

4. The disposable absorbent article defined by claim 1, wherein the void is elongated in the longitudinal direction or in the transverse direction.

5. The disposable absorbent article defined by claim 1, wherein the void comprises at least one void elongated in the longitudinal direction or at least one void elongated in the transverse direction.

6. The disposable absorbent article defined by claim 1, wherein the void comprises a plurality of segments spaced one from another in the longitudinal direction.

7. The disposable absorbent article defined by claim 1, wherein the display area is configured to exhibit color change upon contact with at least one of moisture and bodily fluids.

8. The disposable absorbent article defined by claim 2, wherein the second waist region is formed with an engaging member configured to be engaged with the first waist region.

9. A composite disposable absorbent article comprising a plurality of disposable absorbent articles each as defined by claim 1,
    wherein the disposable absorbent articles are different in size and are stacked in the thickness direction,
    wherein
    a first disposable absorbent article of the disposable absorbent articles having the largest length dimension is positioned closest to the garment-facing side of the composite disposable absorbent article,
    a second disposable absorbent article of the disposable absorbent articles having the smallest length dimension is positioned closest to the skin-facing side of the composite disposable absorbent article, and
    any of the disposable absorbent articles stacked in between said first and second disposable absorbent articles are sized in an order of length dimension such that, in the composite disposable absorbent article, the lengths of the stacked disposable absorbent articles in the longitudinal direction decrease from the garment-facing side to the skin-facing side.

10. The disposable absorbent article defined by claim 1, wherein the display area is elongated in the longitudinal direction.

11. The disposable absorbent article defined by claim 1, wherein the display area extends across a full length of the chassis in the longitudinal direction.

12. The disposable absorbent article defined by claim 10, wherein the display area continuously and rectilinearly extends in the longitudinal direction.

13. The disposable absorbent article defined by claim 3, wherein the region in which the void and the display area coincide with each other exhibits a total luminous transmittance at 30 to 80%.

14. The disposable absorbent article defined by claim 1, wherein the display area extends along at least one of a longitudinal centerline and a transverse centerline of the chassis.

15. The disposable absorbent article defined by claim 1, wherein a dimension of the display area in at least one of the longitudinal direction and the transverse direction is greater than that of the void.

16. The disposable absorbent article defined by claim 2, wherein the display area is visually recognizable through the void in the liquid-absorbent structure and in the at least one of the first and second waist regions to define a reference line configured to be aligned with a wearer's body when worn.

17. The disposable absorbent article defined by claim 1, wherein
the chassis includes a liquid-pervious inner sheet above the liquid-absorbent structure on the skin-facing side, and an liquid-impervious outer sheet below the liquid-absorbent structure on the garment-facing side,
the liquid-impervious outer sheet includes a first outer sheet and a second outer sheet, and
the display area is arranged between the first and second outer sheets in the thickness direction.

18. The disposable absorbent article defined by claim 17, wherein
the second outer sheet is closer to the liquid-absorbent structure than the first outer sheet in the thickness direction, and
the display area is located on the garment-facing side of the second outer sheet.

\* \* \* \* \*